United States Patent [19]

Sobek et al.

[11] Patent Number: 4,869,905

[45] Date of Patent: Sep. 26, 1989

[54] METHOD OF MAKING AND A SLOW RELEASE COMPOSITION FOR ABATING ACID WATER FORMATION

[75] Inventors: Andrew A. Sobek, Fairlawn; Eric Reutern, Marietta; Jerry B. Pausch, Northfield, all of Ohio

[73] Assignee: The B. F. Goodrich Company, Akron, Ohio

[21] Appl. No.: 49,061

[22] Filed: May 12, 1987

[51] Int. Cl.⁴ ............................................. A01N 25/32
[52] U.S. Cl. ................................... 426/406; 424/405; 424/409
[58] Field of Search ................. 424/406, 405, 409, 486

[56] References Cited

U.S. PATENT DOCUMENTS

| | | | |
|---|---|---|---|
| 4,145,408 | 3/1979 | Laughlin | 424/450 X |
| 4,193,983 | 3/1980 | Ulman et al. | 424/450 |
| 4,314,966 | 2/1982 | Kleinmann | 424/19 |

OTHER PUBLICATIONS

"Developments in Controlled Release Technology and Its Application in Acid Mine Drainage", by L. A. Fox and V. Rastogi, 1983 Symposium on Surface Mining, Hydrology, Sedimentology and Reclamation, Nov. 27-Dec. 2, 1983.

"Laboratory Methods for Determining the Effects of Bactericides on Acid Mine Drainage", by Mark A. Shellhorn and V. Rastogi, 1984 Symposium on Surface Mining, Hydrology, Sedimentology, and Reclamation, Dec. 2-27, 1984.

"Use of Controlled Release Bactericides for Reclamation and Abatement of Acid Mine Drainage", by Andrew A. Sobek, Mark A. Shellhorn, and Vijay Rastogi, preprint of Presentation to the International Mine Water Congress, Granada, Spain, Sep. 17-21, '85.

"The Effects of Particle Size Distribution on the Rate of Mine Acid Formation and Its Mitigation by Bacterial Inhibitors", by Mark A. Shellhorn, Andrew A. Sobek, and Vijay Rastogi, American Society of Surface Mining & Reclamation, Denver, Colo., Oct. 8-10, 1985.

"Effect of Bactericide Treatments on Metalliferrous Ore Tailings", by Andrew A. Sobek, Vijay Rastogi, and Mark A. Shellhorn, Society for Surface Mining & Reclamation, Mar. 17-20, 1986, Jackson, Miss.

"ProMac Systems for Reclamation and Control of Acid Production in Toxic Mine Waste", by Vijay Rastogi, Richard Krecic, and Andrew Sobek, Surface Mine Drainage Task Force Symposium, Mar. 31-Apr. 1, 1986.

Primary Examiner—Thurman K. Page
Attorney, Agent, or Firm—James R. Lindsay; Daniel J. Hudak

[57] ABSTRACT

Various chemolithotrophic bacteria such as *Thiobacillus ferrooxidans* by direct or indirect mechanisms catalyze the oxidation of metal sulfides and produce acid, i.e. sulfuric acid and soluble metal salts at a much faster rate than chemical oxidation. Elimination of such bacteria would inhibit the formation of the acid. The natural production of such acids is particularly troublesome in mines e.g. coal mines, since acid water is produced which is damaging to the environment. An effective method of abating or eliminating such acid water production is to apply a bactericide such as a biodegradable organic surfactant which at low pH values are bactericides and hence inhibit the bacteria from catalyzing the metal sulfides. The affected acid water site can thus be treated with the surfactant which provides a temporary or short term result usually for a few months. A long term solution, that is 1 year to several years, is provided through the use of a slow release composition of the present invention in which a heterogeneous matrix contains a thermoplastic domain and an organic surfactant domain. A suitable porosity is created when proper amounts of surfactant are utilized so that a long term slow release composition is formed. A method of making the heterogeneous matrix or slow release composition involves the dry blending of a thermoplastic compound and various processing aids, subsequently adding a bactericide thereto and mixing under shear and heat the resulting molten composition. A suitable slow release article can be formed such as pellets.

23 Claims, No Drawings

METHOD OF MAKING AND A SLOW RELEASE COMPOSITION FOR ABATING ACID WATER FORMATION

FIELD OF THE INVENTION

This invention relates to a composition as well as to a method for providing slow release compositions containing an organic surfactant which inhibits acid producing bacteria from catalyzing metal sulfides such as iron sulfide.

BACKGROUND OF THE INVENTION

U.S. Pat. No. 4,314,966 to Kleinmann relates to a rubber matrix containing a surfactant therein to inhibit the bacteria *Thiobacillus ferrooxidans*.

"Developments in Controlled Release Technology and Its Application in Acid Mine Drainage", by L. A. Fox and Vijay Rastogi, 1983 Symposium on Surface Mining, Hydrology, Sedimentology and Reclamation, Nov. 27 - Dec. 2, 1983, relates to controlling acid mine drainage wherein rubber matrix as well as a thermoplastic matrix, for example polyethylene, were utilized in association with anionic detergents such as sodium lauryl sulfate.

"Laboratory Methods for Determining the Effects of Bactericides on Acid Mine Drainage", by Mark A. Shellhorn and Vijay Rastogi, 1984 Symposium on Surface Mining, Hydrology, Sedimentology, and Reclamation, Dec. 2-7, 1984, relates to laboratory tests wherein surfactants were utilized to control acid-producing bacteria.

"Use of Controlled Release Bactericides for Reclamation and Abatement of Acid Mine Drainage", by Andrew A. Sobek, Mark A. Shellhorn, and Vijay Rastogi, preprint of Presentation to the International Mine Water Congress, Granada, Spain, Sept. 17-21, 1985, relates to tests controlling acid mine drainage through the use of surfactants as well as control release compositions.

"The Effects of Particle Size Distribution on the Rate of Mine Acid Formation and its Mitigation by Bacterial Inhibitors", by Mark A. Shellhorn, Andrew A. Sobek, and Vijay Rastogi, American Society of Surface Mining & Reclamation, Denver, Colo., Oct. 8-10, 1985, relates to the effect of particle size of metal sulfide refuse on acid water production.

"Effect of Bactericide Treatments on Metalliferrous Ore Tailings", by Andrew A. Sobek, Vijay Rastogi, and Mark A. Shellhorn, Society for Surface Mining & Reclamation, Mar. 17-20, 1986, Jackson, Miss., relates to bactericide treatments of uranium, copper, nickel, etc. tailings.

"ProMac Systems for Reclamation and Control of Acid Production in Toxic Mine Waste" by Vijay Rastogi, Richard Krecic, and Andrew Sobek, Surface Mine Drainage Task Force Symposium, March 31 - Apr. 1, 1986, relates to a system utilizing surfactants to treat a reclaimed area.

SUMMARY OF THE INVENTION

Accordingly, it is an aspect of the present invention to provide a method of making and a controlled release surfactant bactericide composition to control acid production in active and/or reclaimed mines.

It is yet another aspect of the present invention to provide a controlled release surfactant bactericide, as above, wherein said surfactant is generally a biodegradable organic anionic surfactant.

It is a further aspect of the present invention to provide a controlled release surfactant bactericide, as above, wherein said controlled release surfactant bactericide is contained in a thermoplastic matrix having a low softening point.

It is a still further aspect of the present invention to provide a controlled release surfactant bactericide, as above, wherein the slow release bactericide is a heterogeneous blend of the thermoplastic compound and the surfactant bactericide.

It is yet another aspect of the present invention to provide a controlled release surfactant bactericide, as above, wherein said thermoplastic matrix has a suitable porosity so that release of said surfactant bactericide is over an extended period of time.

It is yet another aspect of the present invention to provide a controlled release surfactant bactericide, as above, wherein the slow release thermoplastic matrix is formed by dry blending the thermoplastic and at least one compounding agent, and subsequently mixing and shearing a molten mass thereof containing the surfactant bactericide therein.

It is yet another aspect of the present invention to provide said slow release thermoplastic matrix in the form of pellets by extruding said molten mass and pelletizing the same.

These and other aspects of the present invention will become apparent from the following detailed description.

In general, a slow release composition for reducing acid water formation from a metallic sulfide material exposed to water and an acid catalyzing bacteria, comprises a heterogeneous matrix containing a theromplastic domain and a surfactant domain, said thermoplastic domain made from a thermoplastic material, said surfactant domain made from an effective concentration of an organic surfactant inhibiting acid forming bacteria so that said heterogenous matrix has a porosity capable of extended slow release upon contact with water.

DETAILED DESCRIPTION OF THE INVENTION

The controlled release composition of the present invention comprises a blend of thermoplastic compound with an immiscible surfactant bactericide so that the resultant thermoplastic matrix has a porosity capable of extended long term release of the surfactant. By "controlled release" it is meant that the release rate and/or duration of release of the surfactant can be varied. The thermoplastic compound utilized to form the matrix can generally be any thermoplastic polymer which is not degraded at processing temperatures and is compatible, that is accepts the surfactant. Inasmuch as many surfactant bactericides degrade at temperatures at about 211° C. or even less, the Vicat softening point of the thermoplastic compound is generally 210° C. or less, desirably 150° C. or less, and preferably 110° C. or less. Various suitable thermoplastic compounds include polypropylyene, polystyrene, styrene-butadiene-styrene triblock copolymers such as the various Kraton block copolymers manufactured by Shell, polyester, polyurethane, nylon, polyvinyl chloride, ethylene-vinylacetate copolymers and polyethylene. While the ethylene-vinylacetate copolymers are a desired thermoplastic, the various low melting point polyethylenes are preferred such as those that have a Vicat softening point at a temperature of from about 60° C. to about 90° C. The various other components of the present invention are generally based upon 100 parts by weight of the thermoplastic material.

In the reclamation or treating of various metal sulfides, and especially iron sulfide, acid forming bacteria such as *Thiobacillus ferrooxidans* catalyze the oxidation of metal sulfides and produce acids as well as soluble metals. Over a period of time, a considerable acid content can build up. Such buildup is usually in association with various earth disturbance activities including earth mines as well as surface mines since large amounts of the various sulfides are available. Such acid buildup is undesirable in that it is damaging to the ecology in that it prevents vegetation from sprouting and growing as well as killing existing vegetation, causing erosion and sedimentation problems down stream, and the acid itself causing destruction of aqueous life. The production of the acid must generally be prevented for at least three years or more to break the acid production cycle and to permit three main natural biological processes to occur; that is (1) a healthy root system which competes for both oxygen and moisture with the acid producing bacteria, (2) populations of beneficial heterotrophic soil bacteria and fungi are reestablished, resulting in the formation of organic acids which are inhibitory to *Thiobacillus ferrooxidans*, and (3) the action of plant-root respiration and the heterotrophic bacteria which increase $CO_2$ levels in the soil resulting in an unfavorable microenvironment for growth of *Thiobacillus ferrooxidans*.

In order to permit ground cover to continue to grow or reestablish itself, a surfactant bactericide, that is a biodegradable organic surfactant inhibitory to acid producing bacteria such as *Thiobacillus ferrooxidans*, is utilized in the thermoplastic matrix. Generally, cationic and especially anionic surfactants are very effective biocides with regard to acid producing bacteria. Considering the cationic surfactants, examples of such suitable surfactants include cocodimethylbenzylammonium chloride and N(acylocolaminoformylmethyl)-pyridinium chloride. The anionic surfactants and salts thereof, especially sodium, are preferred. A group of preferred anionic surfactants are the various linear alkylbenzene sulfonates (LAS) as for example dodecylbenzene sulfonate, and the like. Especially preferred compounds of the present invention are the sodium salts of alkylbenzene sulfonic acid containing a combination of different alkyl chain lengths having a typical average of approximately 11.8 or 12, such salts having an alkyl average length of approximately 13 and such sodium salts having approximately an average alkyl chain length of 14. Generally the alkyl chain can have from about 9 to about 18 carbon atoms.

Another group of suitable anionic surfactants which function as effective bactericides are the various alkyl sulfates and sodium salts thereof wherein the alkyl group has from about 12 to 18 carbon atoms. Another suitable anionic surfactant is the various alpha olefin sulfonates wherein the total number of carbon atoms is from about 16 to about 20, and the sodium salts thereof. Yet another suitable surfactant bactericide is the various secondary alkane sulfonates having a total number of about 14 to about 18 carbon atoms. The various alcohol ethoxy sulfates constitute another suitable anionic surfactant bactericide wherein the total number of carbon atoms is from about 12 to about 22 carbon atoms. Another suitable bactericide is the various alkylphenol ethoxylates having a total number of from about 18 to about 72 carbon atoms. The various alcohol ethoxylates can also be utilized as suitable surfactant bactericides containing a total number of from about 14 to about 58 carbon atoms.

It is to be understood that various salts of the above surfactants and especially sodium salts can be utilized. The various alkyl surfates constitute a desired group such as sodium lauryl sulfate with the linear alkylbenzene sulfonates constituting a preferred group.

Still other anionic surfactants include a 1 to 18 carbon atom alkyl-phenoxy benzene disulfonic acid; an alkyl- or alkenyl phenoxy benzene disulfonic acid where the alkyl-and alkenyl-groups are $C_8$–$C_{16}$; naphthalene sulfonic acid, alkyl-naphthalene sulfonic acid, or alkenyl-naphthalene sulfonic acid, especially where the alkyl- or alkenyl- groups have relatively short chain lengths, of $C_8$ or below and preferably $C_1$–$C_4$.

A list of various other cationic as well as anionic surfactants can be found in the 1978 annual edition or the 1983 annual edition of McCutcheon's Detergents and Emulsifiers, North American Edition, which is hereby fully incorporated by reference.

The surfactants are blended with the thermoplastic compounds at specific concentrations to produce a slow release composition or matrix at temperatures below the degradation point of the surfactant and yet at temperatures above the softening point of the thermoplastic compound. That is, a matrix is formed having distinct phases therein, a continuous thermoplastic phase or domain and a surfactant phase. The surfactants are generally immiscible with the thermoplastic compound and hence release of the surfactant occurs through elution, that is through solubility and hydrostatic pressure. A heterogeneous matrix is thus formed having a pore structure therein formed by the surfactant bactericide. The resulting porosity, that is the amount of pore structure formed within the theromplastic matrix by the surfactant bactericide is important and critical to effective slow release rates in order to achieve release over an extended period of time. In other words, long term leaching of the surfactant is achieved upon contact with water with a surfactant filled porous network within the thermoplastic matrix. Naturally, the thermoplastic matrix is formed by mixing the thermoplastic compound and the surfactant compound in a manner as described hereinbelow and forming an article therefrom such as a pellet.

According to the concepts of the present invention, it has been found that a suitable porosity for long term release, that is generally at least 1 or 2 years, desirably at least 3 to 5 years, and preferably at least 5 years, can be achieved by the utilization of desired amounts of the surfactant. Thus, a maximum amount of surfactant is approximately about 150 parts by weight or less for every 100 parts by weight of a thermoplastic compound. The concentration of the surfactant can vary to approximately 5 parts by weight based upon 100 parts by weight of the thermoplastic compound. A desired range is from about 25 parts to about 120 parts by weight, and preferably from about 35 parts to about 50 parts by weight per 100 parts by weight of the thermoplastic compound. Generally, the slow release will vary with the type of thermoplastic compound utilized and especially with the concentration of the surfactant. Smaller amounts or concentrations of the surfactants form a smaller porous network or porosity and result in longer release periods. Generally, approximately 50 parts by weight of surfactant will result in a release period of about 2 to 5 years whereas smaller amounts such as about 25 to about 35 parts by weight will result in release periods of approximately 5 to 10 years.

The slow release composition of the present invention is added to a particular environment to effectively control, that is to retard the formation of acid water. Naturally, the amount of acid water varies with the amount of metal sulfide present such as iron sulfide, and the like, the amount of water drainage, oxygen, bacteria, and the like. An effective amount of slow release material added to a specific site area is site specific and based upon hydrology, topography, climatic factors, and physical and chemical parameters of the site material. Such effective amounts can be from about 10 lbs. to about 425 lbs. by weight of surfactant per acre foot and more desirably from about 90 lbs. to about 200 lbs. per acre foot.

The application of the slow release thermoplastic composition of the present invention will retard or substantially eliminate acid water for extended periods of time such that ground cover or vegetation can commence growth and take a sufficient foothold whereby the natural biological processes of the vegetation will break the acid production cycle, as noted hereinabove.

In order to aid in initially abating or eliminating the production of the acid producing bacteria such as *Thiobacillus ferrooxidans*, an initial application of only a surfactant, is applied to the specific site, area, etc. The amount of such surfactant bactericide which is generally the same type of surfactant set forth hereinabove and thus is hereby fully incorporated by reference, is an amount of matrix containing from about 7 lbs. of surfactant to about 300 lbs. of surfactant per acre foot, and desirably from about 45 lbs. to about 150 lbs. of surfactant per acre foot. In other words, an amount of matrix material is utilized such that the weight of surfactant therein is generally within the above ranges.

The method of application of the raw surfactant can be in any conventional manner as by spraying a solution and/or spreading in a wet or dry form.

The slow release composition of the present invention is made by mixing the various ingredients in a manner as set forth hereinbelow. The composition is then generally extruded and pelletized. Accordingly, various compounding ingredients can be used to aid in the mixing and extruding of the slow release composition. Such compounding aids are generally known to the compounding and extruding art and can be used in conventional amounts. Thus, various antioxidants can be utilized such as hindered phenols to aid in preventing degradation of the polymer matrix and the surfactant. Various conventional types of pigments such as titanium dioxide, carbon black, and the like can be utilized in small amounts in order to achieve a desired color of hue so as to color code various concentrations or porosities.

Processing aids such as lubricants, silicas, and fluxing agents are utilized to optimize mixing and processing operations. Suitable lubricants which also control dust problems include high grade mineral oils, polymer processing oil, and the like. The amount thereof is usually quite small, as 1 or 2 parts by weight per 100 parts by weight of thermoplastic compound. Examples of suitable silicas include amorphous silica, and the like, and are utilized in sufficient amounts to provide processing control and usually from about 1 to about 20 parts by weight per 100 parts by weight of the thermoplastic compound. Examples of suitable fluxing agents include stearic acid, calcium stearate, or other lubricants, and the like in suitable amounts to provide for release of compounds from metal surfaces of processing equipment as from about a total of 1 to about 4 parts by weight per 100 parts by weight of the thermoplastic compound.

The slow release thermoplastic composition of the present invention is prepared in the following manner. The thermoplastic such as polyethylene is added to a mixer such as a ribbon blender along with all of the miscellaneous ingredients or compounding agents to form a preblend. Thus, the various pigments, lubricants, antioxidants, and processing aids such as stearic acid and talc are added to the ribbon blender. The various components are added dry in that it is imperative that dry blending occur to enable efficient mixing of the ingredients. The preblend is desirably mixed at ambient temperature.

The preblend is subsequently added to a temperature controlled mixer such as a Banbury. The surfactant of the present invention along with any silica is also added and mixer under heat at approximately 190° F. to about 280° F., such as about 220° F. High temperatures are avoided to minimize thermal degradation and permit better process control. The temperature controlled mixer incorporates the added ingredients into the preblend. Mixing continues until completed whereupon the composition is dumped or added to a two-roll mill or extruded. To obtain additional mixing, typically one of the rolls, for example the back roll, turns at a high rate of speed but is cool, that is has a temperature of from about 50° F. to about 100° F. with approximately 70° F. being preferred. The remaining roll turns at a lower or slow rate of speed, for example the front roll, but is heated to a higher temperature as from about 140° F. to about 200° F. with approximately 160° F. being preferred. Alternatively, the back roll can be hot and the front roll can be cool. The milling ensures that the various components are thoroughly mixed together albeit separate and distinct phases, that is different domains exist inasmuch as the surfactant is immiscible in the thermoplastic compound. After sufficient mixing has occurred, a portion of the material from the first two-roll mill, for example a ribbon of material is fed to a second two-roll mill which is operating under the same conditions as the initial two-roll mill. Hence, the second mill has a fast roll and a slow roll with one roll being operated at a lower temperature than the remaining roll. After a sufficient amount of time on the second mill to obtain uniformity, the heterogeneous immiscible but thoroughly mixed composition is fed as a ribbon of material into an extruder. The majority portion of the extruder is operated at a relatively low temperature as from about 80° F. to 150° F. with about 100° F. being preferred which is approximately the incoming temperature of the ribbon. Upon entering the extruder, the temperature of the composition is gradually heated as it passed therethrough until it reaches a face plate. In the preferred embodiment of the present invention, a hot melt die face plate pelletizer is utilized which is operated at a temperature of about 250° F., although it can be from about 180° F. to about 300° F. Upon passing through the die face plate pelletizer, it is sheared by rotating blades whereby pellets are formed. The pellet size is a function of the diameter of the apertures in the face plate, the ejection pressure of the extrudate, the flow rate of the extrudate, the extruder temperature, the rotational speed of the shearing blades, as well as the slow release formulation. The formed pellets are cooled and conveyed by water at a temperature of from about 60° F. to about 150° F. with approximately 85° F. being preferred. The preferred method of cooling however is by air.

The size of the pellets can generally range from about 0.1 inch to about 1.0 inch. A desirable pellet size with regard to slow release properties and sufficient surface area is a cylinder approximately ¼" in diameter and ¼" in length.

Another or alternative method of forming a slow release thermoplastic composition is to generally add all of the various components together and mix in the presence of heat at a temperature above the softening point of the thermoplastic compound and then to subsequently form a desired article. Thus, a porosity forming surfactant as set forth hereinabove in a suitable or effective amount can be added to a mixer such as a Banbury along with a thermoplastic compound, as noted hereinabove, along with the various compounding agents. It is noted that only one compounding agent need be utilized which is a lubricant processing aid such as stearic acid, calcium stearate, and the like. The temperature of the mixer, as noted, is above the softening point of the thermoplastic compound. Mixing under heat generally continues a suitable amount of time such that a uniformity of the various components is achieved. Thus, a porous forming network is formed by the surfactant throughout the thermoplastic matrix upon cooling of the mixture. That is, upon use of the thermoplastic composition, the surfactant will be removed thereby leaving a porous thermoplastic matrix. The molten mass from the mixer is then generally formed into a convenient article by any suitable forming apparatus. For example, the heated composition can be dropped or added to a compression molding machine wherein bricketts, pellets, and the like are formed. The amounts of the various components is as set forth hereinabove as is the desired release times of the formed article.

The invention will be better understood by reference to the following examples:

EXAMPLE I

Example I had the following formulation:

| MATERIAL | AMOUNT |
| --- | --- |
| Sodium dodecylbenzene sulfonate; carbon chain $C_9$–$C_{13}$ | 37.5 lbs. |
| For example, NACCONOL 90G, from The Stepan Co. | |
| Polyethylene | 100.0 lb. |
| For example, PETROTHENE NA270-00, from U.S. Industrial Chem. Co. | |
| 1,2-Bis(3,5-Di-Tert-Butyl-4-Hydroxyhydrocinn-amoyl)Hydrazine | 0.5 lb. |
| For example, IRGANOX MD-1024, from Ciba-Geigy Corp. | |
| Petroleum Oil | 1.0 lb. |
| For example, SHELLFLEX 371, from Shell Oil Co. | |
| Amorphous Silica | 8.0 lb. |
| For example SYLOX 2, from W. R. Grace & Co. | |
| TALC | 2.0 lb. |
| For example, MISTRON VAPOR TALC from Cyprus Mineral Co. | |
| Stearic Acid | 1.0 lb. |
| For example, EMERSOL-132, from Emery Chem. | |
| Yellow Pigment | 0.2 lb. |
| For example, LR 6475, 80% yellow 42, 20% polyethylene, from Lancer Dispersion, Inc. | |

The above formulation was prepared in pellets of approximately ¼ inch by ¼ inch in a manner as set forth hereinabove, which is hereby fully incorporated. That is, all of the ingredients with the exception of the silica and the sodium dodecylbenzene sulfonate were added to a ribbon blender and blended. Subsequently, the silica and the sodium dodecylbenzene sulfonate were added and mixed. The pellets produced were added to distilled water and the number of hours to 50% extraction of the surfactant contained in the slow release composition is set forth in Table I as is the expected pellet life. The actual life in the earth's environment is much longer since release occurs at a much slower rate.

EXAMPLE II

Example II contained the following formulation:

| MATERIAL | AMOUNT |
| --- | --- |
| Sodium dodecylbenzene sulfonate; carbon chain $C_9$–$C_{13}$ | |
| For example, NACCONOL 90G, from The Stepan Co. | |
| Polyethylene | 100.00 lb. |
| For example, PETROTHENE NA270-00, from U.S. Industrial Chem. Co. | |
| 1,2-Bis(3,5-Di-Tert-Butyl-4-Hydroxyhydrocinn-amoyl)Hydrazine | 0.5 lb. |
| For Example, IRGANOX MD-1024, from Ciba-Geigy Corp. | |
| Petroleum Oil | 1.00 lb. |
| For example, SHELLFLEX 371, from The Shell Oil Co. | |
| Amorphous Silica | 8.00 lb. |
| For example, SYLOX 2, from The W. R. Grace & Co. | |
| TALC | 2.00 lb. |
| For example, MISTRON VAPOR TALC from Cyprus Minerals Co. | |
| Stearic Acid | 1.00 lb. |
| For example, EMERSOL-132, from Emery Chemicals | |
| Phthalocyanine | 0.052 lb. |
| For Example, Q-5755 MUPCO 50% PHTHALO Blue RS, from Ciba-Geigy Corp. | |

This above formulation was made into a slow release thermoplastic composition in a manner as set forth in Example I. When subjected to distilled water, the hours to 50% extraction of the surfactant and the expected release life are set forth in Table I.

RUBBER CONTROL

In a manner as set forth in U.S. Pat. No. 4,314,966 to Kleinmann, which is hereby fully incorporated by reference, a rubber matrix was prepared having the following formulation:

| MATERIALS | PARTS BY WEIGHT |
| --- | --- |
| Natural Rubber | 50 parts |
| SBR | 50 parts |
| Carbon Black | 10 parts |
| Sodium Lauryl Sulfate | 40 parts |

The above rubber formulation when prepared into a slow release composition was tested in distilled water in the same manner as Examples I and II. The time to 50% extraction as well as expected life is set forth in Table I.

TABLE I

| EXAMPLE | CONCENTRATION-PARTS OF SURFACTANT PER 100 PARTS OF POLYETHYLENE | HOURS TO 50% EXTRACTION OF SURFACTANT | EXPECTED LIFE |
| --- | --- | --- | --- |
| I | 37.5 | 478 hours | Greater than 10 years |
| II | 48.3 | 85 hrs. | 3–5 years |
| Rubber Control | 40* | 25 hrs. | 6 mos.–1 year** |

*Based upon 100 parts of rubber
**The rubber degraded (based upon actual field tests)

As readily apparent from Table I, the slow release compositions of the present invention containing a thermoplastic matrix and having a surfactant porosity network therein resulted in much slower release times. That is, release times of anywhere from at least 3 times to about 19 times as long as the rubber control. Moreover, from actual experience, it has been shown that a rubber matrix will not have a release life much beyond 6 months to 1 year since it substantially degrades, whereas the thermoplastic matrixes of the present invention can last up to 100 years or more. Thus, the porosity-forming network of the present invention within the thermoplastic matrix provides a much greater release life.

While in accordance with the patent statutes, a best mode and preferred embodiment has been set forth, the scope of the claims is not limited thereto, but rather by the scope of the attached claims.

What is claimed is:

1. A slow release composition for reducing acid water formation from a metallic sulfide material exposed to water, oxygen, and acid catalyzing bacteria, comprising:
a uniform, immiscible, thoroughly mixed heterogeneous composition containing a thermoplastic domain and a surfactant domain, said thermoplastic domain made from a thermoplastic compound having a softening point of 210° C. or less, said uniform, immiscible, thoroughly mixed heterogeneous composition formed from an effective concentration of an organic surfactant inhibiting acid forming bacteria shear blended in the presence of heat with said thermoplastic compound so that said uniform, immiscible, thoroughly mixed heterogeneous composition has a porosity capable of extended slow release of at least one year upon contact with water, and wherein said effective extended slow release concentration of said organic surfactant is from about 5 parts by weight to about 150 parts by weight per 100 parts by weight of said thermoplastic material.

2. A method of reducing acid water formation from a metallic sulfide containing material exposed to water and acid forming bacteria, comprising:
adding the composition of claim 1 to the metallic sulfide containing material.

3. A slow release composition according to claim 1, wherein the softening point of said thermoplastic compound is 150° C. or less, wherein said thermoplastic is polyethylene, a copolymer of ethylene and vinyl acetate, polypropylene, polystyrene, a styrene-butadiene-styrene triblock polymer, polyester, polyurethane, nylon, polyvinylchloride, and combinations thereof, wherein said surfactant is an anionic surfactant, wherein the amount of said surfactant is from about 25 parts by weight to about 120 parts by weight per 100 parts by weight of said thermoplastic material, and wherein said anionic surfactant is a linear alkylbenzene sulfonate, an alkyl sulfate, an alpha olefin sulfonate, a secondary alkane sulfonate, an alcohol ethoxy sulfate, an alkylphenol ethoxylate, an alcohol ethoxylate, an alkyl phenoxy benzene disulfonic acid, an alkenyl phenoxy benzene disulfonic acid, a naphthalene sulfonic acid, an alkyl-naphthalene sulfonic acid, an alkenyl naphthalene sulfonic acid, or salts thereof.

4. A slow release composition according to claim 3, wherein the softening point of said thermoplastic compound is 110° C. or less, wherein said thermoplastic is polyethylene or a copolymer of ethylene and vinyl acetate, wherein said anionic surfactant is a sodium alkylbenzene sulfonate having an average number of from about 11 to about 14 carbon atoms in said alkyl group or sodium lauryl sulfate, and wherein the amount of said anionic surfactant is from about 35 parts to about 50 parts by weight per 100 parts by weight of said thermoplastic compound.

5. A slow release composition for reducing acid drainage in a pyritic sulfide material which is exposed to water, comprising:
a uniform, immiscible, thoroughly mixed heterogeneous blend of a thermoplastic compound containing a thermoplastic having a softening point of 210° C. or less and an effective concentration of a shear blended *Thiobacillus ferrooxidans* inhibiting anionic surfactant whereby a long-term leachable slow release surfactant filled porous network is formed.

6. A slow release composition according to claim 5, wherein said surfactant filled porous network releases said surfactant for a period of time of at least 1 year, wherein said thermoplastic is polyethylene, a copolymer of ethylene and vinyl acetate, polypropylene, polystyrene, a styrene-butadiene-styrene triblock polymer, polyester, polyurethane, nylon, polyvinylchloride, and combinations thereof, and wherein said anionic surfactant is a linear alkylbenzene sulfonate, an alkyl sulfate, an alpha olefin sulfonate, a secondary alkane sulfonate, an alcohol ethoxy sulfate, an alkylphenol ethoxylate, an alcohol ethoxylate, an alkyl phenoxy benzene disulfonic acid, an alkenyl phenoxy benzene disulfonic acid, a naphthalene sulfonic acid, an alkyl-naphthalene sulfonic acid, an alkenyl naphthalene sulfonic acid, or salts thereof.

7. A slow release composition according to claim 6, wherein said surfactant filled porous network releases said surfactant for a period of time of at least 2 years, and wherein the softening point of said thermoplastic is 150° C. or less.

8. A slow release composition according to claim 7, wherein said surfactant filled porous network releases said surfactant for a period of time of at least 3 years, and wherein the softening point of said thermoplastic is 110° C. or less, wherein said thermoplastic is polyethylene or a copolymer of ethylene and vinyl acetate, and wherein said anionic surfactant is sodium alkylbenzene sulfonate having an average number of from about 11 to about 14 carbon atoms in said alkyl group or sodium lauryl sulfate.

9. A slow release composition according to claim 7, wherein the amount of said anionic surfactant is approximately 50 parts by weight or less per 100 parts by weight of said thermoplastic compound.

10. A method of reducing acid water formation from a metallic sulfide containing material exposed to water and acid forming bacteria, comprising:
adding the composition of claim 8 to the metallic sulfide containing material.

11. A method of reducing acid water formation from a metallic sulfide containing material exposed to water and acid forming bacteria, comprising:
adding the composition of claim 4 to the metallic sulfide containing material.

12. A method of reducing acid water formation from a metallic sulfide containing material exposed to water and acid forming bacteria, comprising:
adding the composition of claim 6 to the metallic sulfide containing material.

13. A method of making a slow release thermoplastic article for inhibiting acid producing bacteria comprising; the steps of,
adding and mixing under heat a thermoplastic compound and an effective amount of a porosity forming surfactant for forming a slow release heterogeneous composition, and
applying shear and mixing said thermoplastic compound and said porosity forming surfactant at a temperature below the degradation temperature of said surfactant, and
forming a thermoplastic article having an extended porosity slow release surfactant.

14. A method according to claim 13, wherein said thermoplastic compound has a softening point of 210° C. or less, wherein said effective amount of a porosity forming surfactant is such that said article has a release life of at least 1 year, and including shearing said slow release composition in a molten state.

15. A method according to claim 14, wherein said thermoplastic compound has a softening point of 150° C. or less, wherein said surfactant is an anionic surfactant, wherein said anionic surfactant is a linear alkylbenzene sulfonate, an alkyl sulfate, an alpha olefin sulfonate, a secondary alkane sulfonate, an alcohol ethoxy sulfate, an alkylphenol ethoxylate, an alcohol ethoxylate, an alkyl phenoxy benzene disulfonic acid, an alkenyl phenoxy benzene disulfonic acid, a naphthalene sulfonic acid, an alkyl-naphthalene sulfonic acid, an alkenyl naphthalene sulfonic acid, or salts thereof, and wherein said effective amount of a porosity forming surfactant is such that said article has a release life of at least 2 years.

16. A method according to claim 15, wherein said thermoplastic compound is polyethylene, a copolymer of ethylene and vinyl acetate, polypropylene, polystyrene, a styrene-butadiene-styrene triblock polymer, polyester, polyurethane, nylon, polyvinylchloride, and combinations thereof, and including pelletizing said molten slow release composition so that said article is a pellet.

17. A method according to claim 16, wherein said thermoplastic compound has a softening point of 110° C. or less, wherein said thermoplastic compound is polyethylene or a copolymer of ethylene and vinylacetate, wherein said surfactant is the sodium salt of a linear alkylbenzene sulfonate wherein said alkyl portion has an average number of carbon atoms of from about 11 to about 14 carbon atoms or sodium lauryl sulfate, and wherein said effective amount of a porosity forming surfactant is such that said pellet has a release life at least 3 years.

18. A method according to claim 14, wherein the amount of said surfactant is 150 parts by weight or less per 100 parts by weight of said thermoplastic compound, and including low shear mixing said molten composition before subjecting said composition to said shear mixing.

19. A method according to claim 15, wherein the amount of said surfactant is 50 parts by weight or less per 100 parts by weight of said thermoplastic compound and including extruding said molten composition and pelletizing said molten composition to form a pelletized composition.

20. A method of making a slow release thermoplastic article for inhibiting acid producing bacteria comprising; the steps of,
adding and mixing under shear at a temperature below the degradation of a porosity forming organic surfactant a thermoplastic compound, an effective amount of the porosity forming organic surfactant capable of inhibiting said acid forming bacteria so that articles made therefrom have an extended surfactant release life, and at least a lubricant processing aid, and
forming a heterogeneous thermoplastic article having a slow release of said surfactant.

21. A method according to claim 20, wherein said thermoplastic compound has a softening point of 210° C. or less, and wherein said effective amount of a porosity forming surfactant is such that said article has a release life of at least one year.

22. A method according to claim 21, wherein said surfactant is an anionic surfactant, wherein said anionic surfactant is a linear alkylbenzene sulfonate, an alkyl sulfate, an alpha olefin sulfonate, a secondary alkane sulfonate, an alcohol ethoxy sulfate, an alkylphenol ethoxylate, an alcohol ethoxylate, an alkyl phenoxy benzene disulfonic acid, an alkenyl phenoxy benzene disulfonic acid, a naphthalene sulfonic acid, an alkyl-naphthalene sulfonic acid, an alkenyl naphthalene sulfonic acid, or salts thereof, and wherein said effective amount of said surfactant is from about 25 parts by weight to about 120 parts by weight per 100 parts by weight of said thermoplastic compound.

23. A method according to claim 22, wherein said thermoplastic compound has a softening point of 150° C. or less, wherein said thermoplastic compound is polyethylene or a copolymer of ethylene and vinylacetate, wherein said surfactant is the sodium salt of a linear alkylbenzene sulfonate, wherein said alkyl portion has an average number of carbon atoms of from about 11 to about 14 carbon atoms or sodium lauryl sulfate, and wherein said amount of said surfactant is such that said article has a release life of at least 3 years.

* * * * *